United States Patent

Crute

[11] Patent Number: 5,958,696
[45] Date of Patent: Sep. 28, 1999

[54] QUANTITATIVE SOLID PHASE HELICASE ASSAY

[75] Inventor: James J. Crute, Danbury, Conn.

[73] Assignee: Boehringer Ingelheim Pharmaceuticals, Inc., Ridgefield, Conn.

[21] Appl. No.: 09/083,478

[22] Filed: May 22, 1998

Related U.S. Application Data

[60] Provisional application No. 60/052,809, Jul. 17, 1997.

[51] Int. Cl.[6] .............................. C12Q 1/68; C12N 9/00; G01N 33/566
[52] U.S. Cl. ................... 435/6; 435/183; 436/501
[58] Field of Search .................. 435/6, 183; 436/501

[56] References Cited

U.S. PATENT DOCUMENTS

| 5,705,344 | 1/1998 | Giordano et al. | 435/6 |
| 5,712,383 | 1/1998 | Sheridan et al. | 536/24.3 |

OTHER PUBLICATIONS

Kolalowski et al. "Comparison of an Intercalating Dye and an Intercalant–Enzyme Conjugate for DNA Detection in a Microtiter–Based Assay", Anal. Chem, vol. 68, pp. 1197–1200 Apr. 1, 1996.

Sambrook et al. Molecular Cloning:A laboratory manual, 2nd 2d. Cold Spring Harbor University Press, p. 4.9, 1989.
Abdel–Monem M., et al. Eur.J.Biochem. (1976) 441–449, 65.
Ventkatesan, M., et al. J. Biol.Chem. (1982) 12426–12434, 257.
Matson, S.W., et al. J.Biol.Chem. (1983) 14017–14024, 258.
Houston,P., and Kodadek, T. Proc.Natl.Acad.Sci.USA (1994) 5471–5474, 91.
Raney,K.D., et al. Proc.Natl.Acad.USA (1994) 6644–6648, 91.

*Primary Examiner*—Lisa B. Arthur
*Assistant Examiner*—Jehanne Souaya
*Attorney, Agent, or Firm*—Robert P. Raymond; Anthony P. Bottino; Alan R. Stempel

[57] ABSTRACT

This invention relates to a solid phase helicase assay for identifying helicase inhibitors. The assay having a model helicase substrate adsorbed on a solid support, the model helicase substrate being an immobilized extended single-stranded nucleic acid polymer hybridized to a labeled helicase reaction product. The presence of the labeled helicase reaction product is detectable in solution on helicase activity. Also described is a method for measuring the helicase inhibiting ability of test substances thus, making the assay useful for identifying pharmaceutically important helicase inhibitors.

10 Claims, 6 Drawing Sheets

QUANTITATIVE SOLID PHASE HELICASE ASSAY

This application claims the benefit of U.S. Provisional Application No. 60/052,809 filed Jul. 17, 1997.

TECHNICAL FIELD OF THE INVENTION

This invention relates to a solid phase assay to measure quantitatively the ability of a test compound to inhibit DNA or RNA helicase activity. This assay advantageously simplifies the quantitation of helicase activity, and is especially well suited for rapid quantitation of large numbers of individual samples. The assays and methods of this invention may be used to identify pharmaceutically important helicase inhibitors.

BACKGROUND OF THE INVENTION

Helicases are mechanochemical enzymes that couple the energy of nucleoside triphosphate hydrolysis to the dehybridization or unwinding of duplex nucleic acid molecules (1). Nucleic acid unwinding is of central importance in a variety of nucleic acid transactions that include the transcription, translation, recombination, and replication of genetic material. The importance of helicases is further underscored by the large number of DNA or RNA helicases identified in prokaryotic and eukaryotic organisms.

Assays that are both rapid and quantitative for the routine measurement of helicase activity have not been available. There have been essentially two types of helicase assays developed to date. One type of assay has relied on the generation of single-stranded, nuclease sensitive molecules from nuclease insensitive, uniformly radiolabeled double-stranded substrates, followed by the quantitation of acid soluble nucleotides (2). Alternatively, helicase activity has been determined by the unwinding of model duplex substrates comprised of a labeled oligonucleotide hybridized to a larger unlabeled single-stranded molecule followed by size separation (3, 4). Because of the difficulty in obtaining assay substrates suitable for performing the first type of assay, the latter assay has been more commonly utilized. The use of model duplex substrates has also generated the greater variety of nucleic acid structures necessary for the detection of activity associated with different classes of helicase enzymes.

Although the construction of model helicase substrates is useful for detecting enzyme-associated helicase activity, the measurement of that activity is unduly tedious when large numbers of assays need to be performed. This is due to the methods commonly employed in the quantitation of helicase reaction products. Helicase reaction products have primarily been separated from substrates by non-denaturing PAGE (4). Alternative methods have included the hybridization of single-stranded helicase-generated nucleic acid molecules to scintillant-containing beads or fluorescence methods based on resonance energy transfer properties of labeled nucleic acid molecules or specific double-stranded DNA dyes (5–8). In one recently published solution phase helicase assay, DNA intercalators were used as an indicator fluorescent dye for double-stranded DNA molecules (8). In that assay, helicase activity was measured by a decrease in fluorescence.

Each of the above-described quantitative methods suffers from individual drawbacks in terms of accuracy, reproducibility, use of special or sophisticated equipment, time required, expense and capacity to measure routinely large numbers of samples for helicase activity.

SUMMARY OF THE INVENTION

This invention overcomes the drawbacks associated with the previous helicase assays by providing a solid phase assay in which the product of the helicase reaction may be readily and quantitatively detected.

The prime objective of this invention is to provide a solid phase assay comprising a model helicase substrate adsorbed on a solid support, wherein the model helicase substrate comprises an immobilized extended single-stranded nucleic acid polymer hybridized to a labeled helicase reaction product, wherein the presence of the labeled helicase reaction product is detectable in solution on helicase activity.

Another objective of this invention is to provide a method for measuring the helicase inhibiting ability of a test substance comprising the steps of:

(a) immobilizing on a solid support a model helicase substrate comprising an extended single-stranded nucleic acid polymer hybridized to a labeled helicase reaction product, wherein the labeled helicase reaction product is detectable in solution on helicase activity;

(b) contacting the immobilized model helicase substrate with a test substance to produce a reaction premix;

(c) contacting the reaction premix of step (b) with a helicase capable of releasing the labeled helicase reaction product into solution on helicase activity; and (d) measuring the amount of labeled helicase reaction product released into solution as a function of time.

A further objective of this invention is to provide inhibitors of helicase activity identified using the assays and methods of this invention.

These and other objectives will be readily appreciated by those of ordinary skill in the art based upon the following detailed disclosure of this invention.

DETAILED DESCRIPTION OF THE INVENTION

Figure 1:
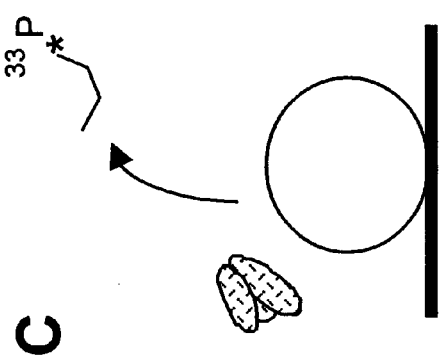
FIGS. 1A, 1B, 1C. Schematic representation of the steps in the solid phase helicase assay. A. Adsorption of radiolabeled model helicase substrates to derivatized surfaces. B. Progression of the helicase reaction. C. Release of soluble, labeled helicase reaction products. Quantitation of the helicase reaction products by scintillation counting reaction mixture aliquots. NTP, nucleoside 5'-triphosphate; NDP, nucleoside 5'-diphosphate. The helicase enzyme is represented as a heterotrimer.
Figure 1:
Figure 1:
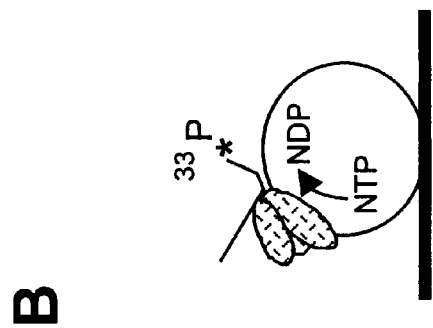
Figure 1:
Figure 1:
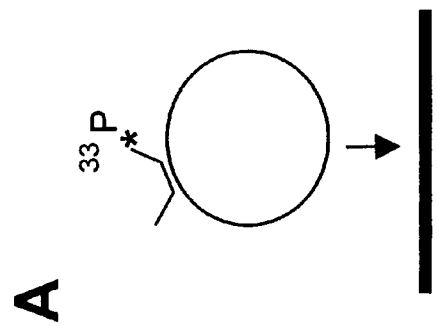

In order that the invention herein described may be more fully understood, the following detailed description is set forth. As used herein, the following abbreviations apply:
ADPβS=adenosine-5'-O-(2-thiodiphosphate)
AMPPCP=adenylyl(β,γ-methylene)-diphosphonate
AMPPNP=adenylyl-imidodiphosphate
ATPγS=adenosine-5'-O-(3-thiotriphosphate)
$BS^3$=bis(sulfosuccinimidyl) suberate
BSA=bovine serum albumin
DTT=dithiothreitol
EGTA=ethylene glycol-bis(β-aminoethyl ether)-N,N'-tetraacetic acid
HSV-1=herpes simplex virus type 1
PAGE=polyacrylamide gel electrophoresis
PBS=phosphate-buffered saline
SDS=sodium dodecyl sulfate
SSB=single-stranded DNA binding protein.
Surfact-Amps 20=Tween 20

The solid phase assay of this invention comprises a model helicase substrate adsorbed on a solid support, wherein the model helicase substrate comprises an immobilized extended single-stranded nucleic acid polymer hybridized to a labeled helicase reaction product, wherein the presence of the labeled helicase reaction product is detectable in solution on helicase activity.

The assays of this invention are particularly well suited for identifying helicase inhibitors. Specifically, the assays of this invention are suitable for use in a method for measuring the helicase inhibiting ability of a test substance such as a test compound comprising the steps of:

(a) immobilizing on a solid support a model helicase substrate comprising an extended single-stranded nucleic acid polymer hybridized to a labeled helicase reaction product, wherein the labeled helicase reaction product is detectable in solution on helicase activity;

(b) contacting the immobilized model helicase substrate with a test substance to produce a reaction premix;

(c) contacting the reaction premix of step (b) with a helicase capable of releasing the labeled helicase reaction product into solution on helicase activity; and (d) measuring the amount of labeled helicase reaction product released into solution as a function of time.

Solid support materials that can be used for this assay include any conventional support materials, including (but not limited to) polystyrene, polyvinyl chloride or polycarbonate microtiter plates or beads and derivatized argarose or acrylamide beads. The preferred support material for the assays of this invention is a polystyrene 96-well microtiter plate. The surface of the solid support material is preferably derivatized with a protein. However, other small DNA-interaction promoting materials (e.g., glycine) may also be used. In general, preferred derivatized surfaces for use in the assay of this invention are characterized by promoting (1) a stable interaction between the derivatized surface and the helicase substrate at acidic pH (i.e., between about 2 and about 5, but preferably between about 3 and about 4.5) and on transfer to neutral pH (i.e., between about 6 and about 8) (see FIG. 2A) and (2) a lack of binding affinity between the derivatized surface and the labeled helicase reaction product at neutral pH or slightly alkaline pH (i.e., between about 8 and about 10) (see FIG. 2B). Derivatized surfaces useful in the assays of this invention include those of cytochrome-C, avidin, streptavidin or glycine. The most preferred derivatized surface for use in the assays of this invention is an avidin-derivatized polystyrene microtiter plate.

The model helicase substrate for use in the assays and methods of this invention comprise two distinct components: (1) an extended single-stranded nucleic acid polymer which is hybridized to (2) a labeled helicase reaction product. The extended single-stranded nucleic acid polymer is further characterized as being adsorbable to the surface of a solid support material while retaining its ability to hybridize to the labeled helicase reaction product under suitable assay conditions. In general, the extended single-stranded nucleic acid polymer according to this invention is adsorbed to the solid support at acid pH and remains adsorbed on transition to neutral pH. Preferred extended single-stranded nucleic acid polymers are circular, single-stranded DNA chains from about 1000 to about 10,000 nucleotides in length (preferably, between about 3000 and about 10,000 nucleotides and more preferably, between about 5,000 and about 10,000 nucleotides in length).

In general, helicases (whatever the native organism) are not sequence specific and will unwind double-stranded nucleic acid polymers (DNA or RNA, depending on the nature of the helicase), regardless of the particular sequence presented. Accordingly, the sequence identity of the extended single-stranded nucleic acid polymer and likewise, the labeled helicase reaction product, may be freely varied, so long as the extended single-stranded nucleic acid polymer conforms to the above noted requirements and the labeled helicase reaction product remains hybridized to the extended single-stranded nucleic acid polymer at acidic pH and is released into and detectable in solution on helicase activity at neutral pH. Preferred model helicase substrates of this invention are optionally double-tailed. In double-tailed model helicase substrates, the labeled helicase reaction product comprises a hybridizing sequence flanked by non-hybridizing sequences on both its 5' and 3' end. Since helicases are directional (i.e., some proceed in the 5'→3' direction while others proceed in the 3'→5' direction), such double tailed model helicase substrates may be more universally utilized because those model helicase substrates can facilitate helicase activity in either the 3' to 5' or the 5' to 3' direction. This type of substrate allows for a high degree of flexibility when performing assays since helicases that require free 3' or 5' fork-like structures may be interchangeably measured. Additionally, helicases not requiring fork-like structures to display activity may also be assayed using a double-tailed model helicase substrate. Preferably, the labeled helicase reaction product for use in the preferred double-tailed model helicase substrates of this invention will have from about 10–about 50 nucleotides (and preferably, from about 15–about 30 nucleotides) in the hybridizing region of its sequence and from about 10–about 80 (preferably, about 15–about 30) non-hybridizing nucleotides flanking both its 3' and its 5' end. FIG. 1A graphically represents such a double-tailed model helicase substrate being immobilized to a solid support.

The preferred model helicase substrate for use in the assays of this invention comprises M13mp19 single-stranded DNA hybridized with the $^{33}$P-labeled 68-mer described in (9) and (10). The $^{33}$P-radiolabeled 68-mer comprises 22 hybridizing nucleotides and 23 non-hybridizing nucleotides flanking the 3' and 5' ends of the hybridizing sequence. The use of a radiolabeled oligonucleotide annealed to M13mp19 single-stranded advantageously allows for the quantitation of unwound substrate by liquid scintillation, counting an aliquot of the assay solution from individual wells. Although this preferred helicase substrate may be used with any DNA helicase, it is especially well suited for measuring helicase activity of a herpes helicase-primase and, more preferably, the HSV-1 helicase-primase.

To assist in detection of the released helicase reaction product, the released helicase reaction product is preferably radiolabeled. Fluorescence and other conventional detection methods may also be used, so long as they are sufficiently sensitive and accurate to meet the needs of the investigator. Appropriate alternate detection methods are well known to those possessing ordinary skill in the art.

The assays and methods of this invention envision the use of RNA-, DNA- or mixed RNA/DNA model helicase substrates. For instance, the extended single-stranded nucleic acid polymer and labeled helicase reaction product may be made of either RNA or DNA. Furthermore, the extended single-stranded nucleic acid polymer may be made of RNA, while the labeled helicase reaction product may be made of DNA (or visa versa). Such DNA/DNA, DNA/RNA, RNA/DNA and RNA/RNA combinations will allow for the study of all types of helicases, including prokaryotic replicative helicases (such as the dnaB protein of *E. coli*) and various eukaryotic helicases. Although the examples described herein utilize the HSV-1 helicase-primase and a DNA/DNA model helicase substrate, it should be recognized that any helicase may be used in the assays and methods of this invention with a model helicase substrate appropriate for that helicase.

According to this invention, the extended single-stranded nucleic acid polymer component of the model helicase substrate is adsorbed to the surface of the solid support material at an acidic pH and that adsorption is not interrupted by a transition to neutral pH. Preferably, the labeled helicase reaction product is hybridized to the extended single-stranded nucleic acid polymer prior to immobilization. The labeled helicase reaction product component of the helicase substrate is released on helicase activity at neutral pH and remains detectable in solution. Advantageously, the released helicase reaction product is not adsorbed onto the support material nor does it rehybridize to the immobilized extended single-stranded nucleic acid polymer under conditions needed to induce helicase activity and to detect the released helicase reaction product. Helicase activity is, therefore, easily and rapidly quantitated by removing aliquots of the reaction solution over a period of time and detecting the presence of released helicase reaction product in the solution. Preferably, the aliquots are removed and analyzed in 30 second–10 minute increments over a 2 hour period. More preferably, the aliquots are removed and analyzed in 5–10 minute increments over a 1 hour period. As one possessing ordinary skill in this art will readily acknowledge, measurements may be made in longer or shorter time increments over a longer or shorter period of time, according to the particular objectives of a given experiment.

Without wishing to be bound by theory, the physical biochemical processes behind the adsorption of model helicase substrates to solid supports is likely to be at least partly hydrophobic in nature, since substrate adsorption is favored at moderate ionic strengths and not prevented at high ionic strengths. There may also be electrostatic interactions that participate in binding the nucleic acid substrates, as acidic pH is optimal for the binding of helicase substrates to protein-derivatized surfaces. The overall positive charge of the derivatized surface of the solid support tends to adsorb the overall negatively charged extended single-stranded nucleic acid polymers. However, even when the ionic interaction is altered (e.g., on addition of salt to the reaction premix), the extended single-stranded nucleic acid polymer does not disassociate from the surface, implicating possible non-ionic (e.g., hydrophobic) interactions.

Activity in the solid phase helicase assay of this invention depends on the addition of a nucleoside triphosphate, generally ATP, to drive the unwinding reaction. In addition, the rate of reaction is mediated by the amount of enzyme added to the reaction premix and the kinetic rate constant of the enzyme. For example, unwinding activity measured in the solid phase helicase assay using the HSV-1 helicase-primase is generally proportional between about 3 and at least 16 pmol of added HSV-1 enzyme and linear with time up to 30 minutes. However, it would be expected that with different rate constants, the rate of unwinding activity might be significantly different. The appropriate parameters (e.g., time intervals, amount of enzyme or test compound used, etc.) can be adjusted by those possessing ordinary skill in the art to arrive at a suitable assay system for a given purpose.

As the following examples demonstrate, the assays and methods of this invention have been used to identify nucleoside-based HSV-1 helicase-primase inhibitors from the commonly available nucleosides AMPPCP, AMPPNP, ADPβS, ADP, and ATPγS. AMPPCP and AMPPNP were found to be ineffective at inhibiting the helicase activity of the HSV-1 helicase-primase, ADPβS was a weak helicase inhibitor, and ADP and ATPγS effectively inhibited helicase activity to near background levels at concentrations of 0.5 mM and 6.0 mM, respectively. Inhibition of the HSV-1 helicase-primase by either ADPβS, ADP, or ATPγS was found to be concentration-dependent. The potency of these nucleoside helicase inhibitors was also analyzed in more traditional helicase assays where substrates were separated from products by non-denaturing PAGE. Results were similar to those found with the solid phase helicase assay, providing a good correlation and further validating the assay of this invention. These results support the hypothesis that these nucleosides inhibit helicase action by competition with the NTP that drives helicase activity.

The inhibitory activity of ADP against the HSV-1 helicase-primase has also been characterized. ADP was a more potent and effective inhibitor when GTP, CTP or UTP was used to drive the helicase reaction when compared to reactions utilizing ATP. Interestingly, the relative effectiveness of each of the four nucleoside triphosphates in supporting helicase activity was identical to their relative abilities to be hydrolyzed by the HSV-1 helicase-primase in DNA-dependent NTPase assays. This observation is again consistent with a mechanism of inhibition wherein ADP competes with the NTP used to drive the helicase reaction.

The solid phase helicase assay of this invention advantageously measures both accurately and quickly the extent to which a test substance inhibits helicase activity. For example, once the microtiter plates used for the assays were avidin-derivatized and helicase substrates adsorbed, the experiments depicted in FIGS. 5 and 6 were assembled, run, and processed in a period of only 2 hours each. As these experiments contain nearly 200 individual helicase reactions, the improvement in efficiency is substantial compared to alternative methods. Further time efficiency could be introduced by using scintillation counters capable of analyzing 96 well plate formats. Helicase reaction solutions could be removed from the solid phase assay plates and directly dispensed to scintillant-containing plates for quantitation. Importantly, this increase in through-put of the solid phase helicase assay does not sacrifice accuracy. All of the assays reported below were performed in triplicate with standard errors less than 5% of the mean values. In fact, in many circumstances the standard errors were less than the size of the points used in data plotting (see FIGS. 3 and 4).

Since the methods described for the solid phase helicase assay are readily carried out and do not require specialized equipment, the assay of this invention should be very useful in the preliminary characterization of new helicases. The experimental methods exemplified and described herein, with or without modifications to adapt to individual helicase systems, will be useful in the identification of inhibitor molecules that may prevent the function of key RNA or DNA helicase(s). The identification of inhibitors specific for these enzymes that are critical for the growth and replication of human pathogens will assist in the generation of new disease-specific therapies.

In order that this invention be more fully understood, the following examples are set forth. These examples are for the purpose of illustrating preferred embodiments of this invention, and are not to be construed as limiting the scope of this invention in any way.

EXAMPLES

Material and Methods

Reagents. Sodium citrate buffers were prepared as 1.0 M stock solutions with citric acid and the pH was adjusted to the indicated value with concentrated NaOH. $NH_2$-activated 96 well plates were obtained from Costar. $BS^3$ and Surfact-Amps 20 were obtained from Pierce. Avidin and streptavidin were from Boehringer Mannheim. PBS was from JRH. Glycine was from Bio-Rad and prepared as a 1.0 M stock solution adjusted to pH 7.4 with NaOH prior to use. Acetylated BSA was obtained from GIBCO-BRL Life Sciences as 50 mg/mL stock solutions. Hepes was from Amersham, DTT was from Calbiochem-Novabiochem Corporation. ATP, GTP, and ADP were obtained in dry form and solutions of CTP and UTP (100 mM, pH 7) from Pharmacia Biotech. AMPPNP, AMPPCP, ATPγS, and ADPβS were from Boehringer Mannheim. Stock solutions of nucleoside phosphates were prepared at 100 mM final concentration and pH adjusted to 7.5 with concentrated $NH_4OH$. When nucleoside phosphates were used as potential helicase inhibitors, solutions were complexed with 1 mol of $MgCl_2$ per mol nucleoside phosphate to avoid altering the free $Mg^{2+}$ levels in individual helicase reactions. ReadySafe liquid scintillation fluid and γ[$^{33}$P]ATP were from DuPont NEN Research Products.

Buffers. Buffer A was 20 mM NaCitrate, pH 4.0; 200 mM NaCl; and 1.0 mM EDTA. Buffer B was 20 mM Hepes, pH 7.5; 200 mM NaCl; 1.0 mM EDTA; 0.04% (v/v) Surfact-Amps 20. Buffer C was 40 mM Hepes, pH 7.5; 10% (v/v) glycerol; 5.5 mM $MgCl_2$; 4.0 mM ATP, 100 μg/mL BSA; 1.0 mM DTT. Buffer D was 20 mM Hepes, pH 7.5; 10% (v/v) glycerol; 200 mM NaCl; 0.1 mM EDTA; 0.1 mM EGTA; and 1.0 mM DTT.

Nucleic acid substrates. M13mp19 single-stranded DNA and the 68-mer oligonucleotide used to assemble the helicase substrates were prepared as follows: Double-tailed helicase substrates were assembled from $^{33}$P labeled 68-mer oligonucleotides and M13mp19 single-stranded DNA exactly as described (9, 10). Following gel filtration the substrates were concentrated by diafiltration to a concentration of 1 to 3 mM in total nucleotide (0.15 to 0.5 μM in circular M13 molecules) (10). The specific activity of the helicase substrate was approximately $1.2 \times 10^{14}$ cpm/mol nucleotide or $7.5 \times 10^{17}$ cpm/mol M13mp19 molecules (e.g. 120 cpm/pmol nucleotide and 750 cpm/fmol M13 molecules, respectively). The specific activity of the single-stranded 68-mer used for oligonucleotide binding studies was $3.3 \times 10^{17}$ cpm/mol 68-mer (e.g. 330 cpm/fmol).

Cells, viruses, proteins. The HSV-1 helicase-primase used in these studies was the three subunit holoenzyme comprised of the UL5, UL8 and UL52 proteins expressed in SF21 cells with previously described recombinant baculoviruses (10, 11). The recombinant enzyme was isolated and stored as described, stock solutions were at a concentration of 1.0 mg/mL (3.4 μM) (10). Avidin and streptavidin were prepared as 1.0 mg/mL solutions in PBS and dialyzed against excess PBS prior to use.

Example 1

Preparation of plates/adsorption of helicase substrates. Activation of the amine-derivatized 96 well plates was with $BS^3$ under conditions described by Costar. After activation for 30 min with $BS^3$ (1 mg/mL in PBS, 250 μL/well), plates were washed three times with excess PBS and derivatized with 150 μL/well of either avidin (10 μg/mL in PBS), streptavidin (10 μg/mL in PBS), glycine (100 mM), or PBS alone. After a period of 1.0 hour at 37° C., of 1.0 M glycine was added to each well and incubation continued for an additional 30 minutes at room temperature. The activated, derivatized plates were then washed two times with PBS and two times with Buffer A. Helicase substrates were diluted with Buffer A to a final concentration of 12 μM in nucleotide (1.9 nM in circular molecules) for subsequent use, the 68-mer oligonucleotide was diluted to a concentration of 4.2 nM (in molecules) prior to use. In all cases, 100 μL of the individual nucleic acid solutions were used for adsorption to the solid supports for a period of 3 to 4 hours at room temperature with shaking in a 100% relative humidity environment. After allowing for nucleic acid adsorption, the plates were washed 3 times with Buffer B. When plates were analyzed for the ability to adsorb nucleic acid molecules, samples were eluted overnight by the application of 200 μL of a solution of 0.2 M NaOH containing 1.0% (w/v) SDS. Quantitation of the adsorbed samples was by scintillation counting after mixing with 800 μL of liquid scintillation fluid. This process eluted ≧95% of the bound DNA (data not shown). When helicase assays were performed, avidin-derivatized helicase substrate-adsorbed plates were used immediately after washing with Buffer B and removal of residual liquid.

Example 2

Assembly of helicase assays. Solid phase helicase assays were assembled on ice with avidin-derivatized 96 well plates to which M13mp19/$^{33}$P-labeled 68-mer hybrid substrates had been adsorbed in Buffer A and then washed with Buffer B (see above). Reaction premixes were prepared on ice in Buffer C. The indicated amount of the HSV-1 helicase-primase per reaction performed was added to each premix as a 1/10$^{th}$ volume aliquot in Buffer D. Each enzyme-containing reaction mixture was then dispensed in triplicate to individual substrate-containing microtiter plate wells (100 μL/well). Helicase reactions were initiated by transfer of the assembled plate(s) onto the surface of a constant temperature water bath maintained at 36 degrees centigrade. After the indicated times either 70 μL samples were removed or the entire helicase assay plate was returned to ice. When helicase reactions were stopped by transfer to ice temperature, samples (70 μL) were again removed. Individual samples were quantitated by liquid scintillation counting after the addition of 800 μL of ReadySafe liquid. The means and standard errors of individual triplicate helicase assays were determined.

Example 3

Figure 2:
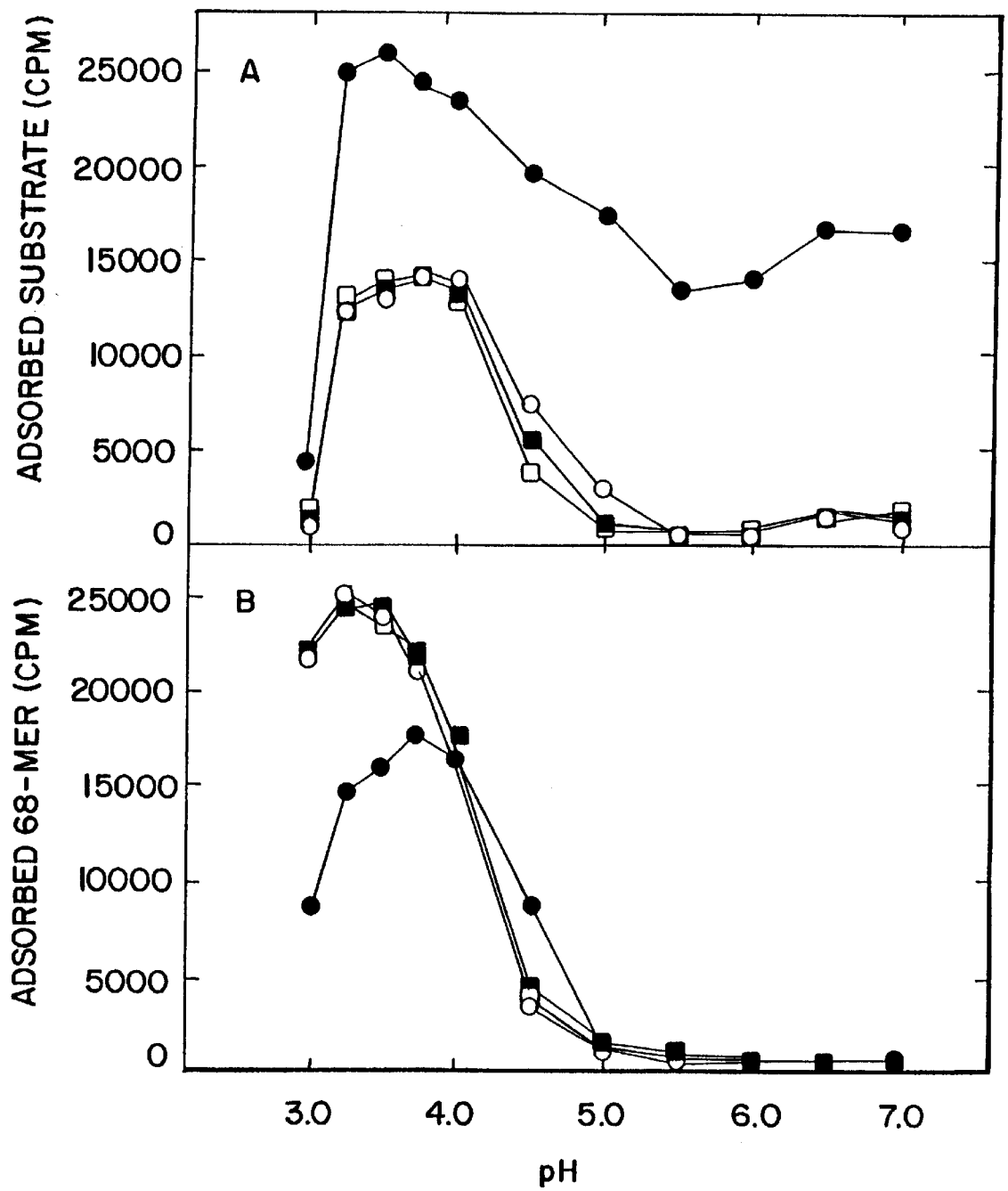
FIGS. 2A, 2B. Adsorption of model helicase substrates and helicase reaction products is pH and surface-dependent. Adsorption of nucleic acids and subsequent quantitation was carried out as described herein, wherein the pH of the citrate buffer used for adsorption was varied between 3.0 and 7.0 as indicated in FIG. 2. Surfaces used were derivatized with avidin (●), streptavidin (○), glycine (□) or PBS (■). Results are the mean of triplicate samples. Adsorption of helicase substrates (A), adsorption of the radiolabeled 68-mer helicase reaction product (B).

Adsorption of helicase substrates and oligonucleotide reaction products is pH-dependent. The model DNA helicase substrate analyzed contained a radiolabeled oligonucleotide with 3' and 5' non-hybridizing sequences when annealed to M13mp19 single-stranded DNA (9). I examined the ability of polystyrene microtiter plates derivatized with various molecules to support the adsorption of assembled helicase substrates comprised of a $^{33}$P-labeled 68-mer hybridized to M13mp19 single-stranded DNA or the labeled 68-mer oligonucleotide product of the helicase reaction by the manipulation of pH. Acidic pH favored the stabile interaction of nucleic acids with the plate surfaces (FIG. 2A). Maximal adsorption of the helicase substrate was observed between pH 3.25 and pH 4.0. Nearly two-fold more substrate was bound by avidin-derivatized surfaces under optimal conditions than surfaces that were streptavidin or glycine derivatized. Under all of the conditions described, once substrates were bound to the surfaces, interactions were not disrupted by transfer to neutral pH.

Surfaces that were cytochrome C-derivatized behaved similarly to streptavidin or glycine-derivatized surfaces; HSV-1 SSB-coated surfaces were found to adsorb little of the input DNA at all pH values examined (data not shown). The adsorptive properties of the avidin-derivatized surfaces were found not as strictly dependent on the pH used for immobilization of the helicase substrates when compared to the other surfaces examined. Optimal substrate binding was still in the acidic pH range indicated above (FIG. 2A). The maximum amount of substrate was bound in the presence of 200 mM NaCl under the adsorption conditions examined. The amount of substrate bound at optimum NaCl concentrations was approximately twice the amount bound in Buffer A without NaCl and 1.5 times the amount bound in Buffer A with the NaCl concentration increased to 1.0 M (data not shown).

The helicase reaction product, the radiolabeled 68-mer oligonucleotide, was also found to stably interact with derivatized surfaces at acidic pH (FIG. 2B). The optimum pH range for binding of the radiolabeled 68-mer was more acidic when compared to the M13mp19/68-mer hybrid. Under optimal conditions, avidin-derivatized surfaces bound less of the 68-mer when compared to the other surfaces examined. Moreover, there was little detectable binding of helicase reaction products at neutral pH values; typical conditions used in helicase reactions. This implied that under conditions used in duplex nucleic acid unwinding assays, the released radiolabeled product of the helicase reaction, the 68-mer, would remain in solution for detection.

Example 4

Figure 3:
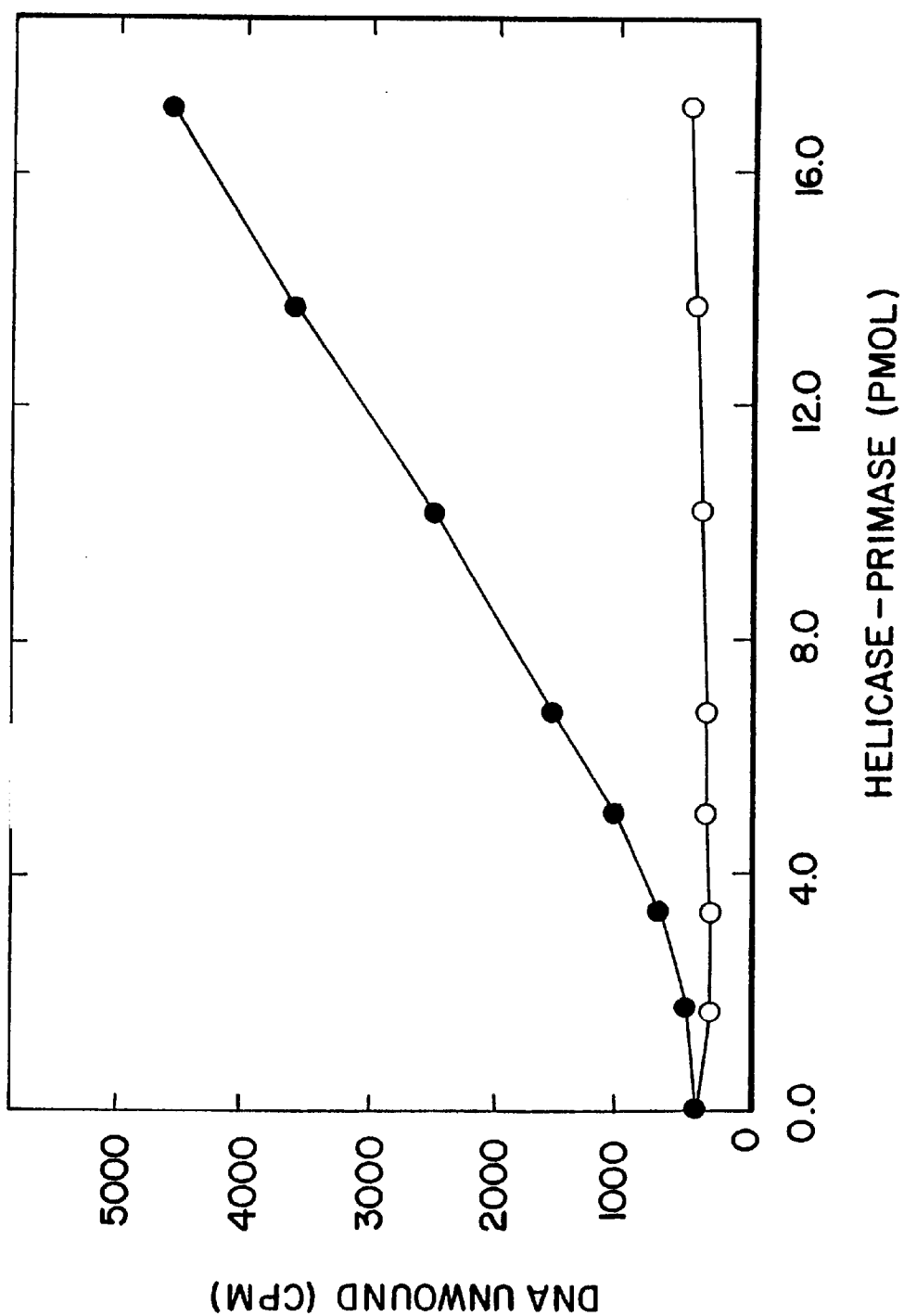
FIG. 3. Helicase enzyme and ATP are required for unwinding of adsorbed duplex substrates. Helicase substrate was adsorbed to avidin-derivatized 96 well plates for helicase reactions. Increasing amounts of the HSV-1 helicase-primase holoenzyme were added as indicated in either Buffer C (●) or Buffer C with ATP deleted (○). Helicase activity was determined after 15 min of reaction time. Results are the mean±standard error of triplicate samples. Note: Error bars do not show beyond the points.
Figure 4:
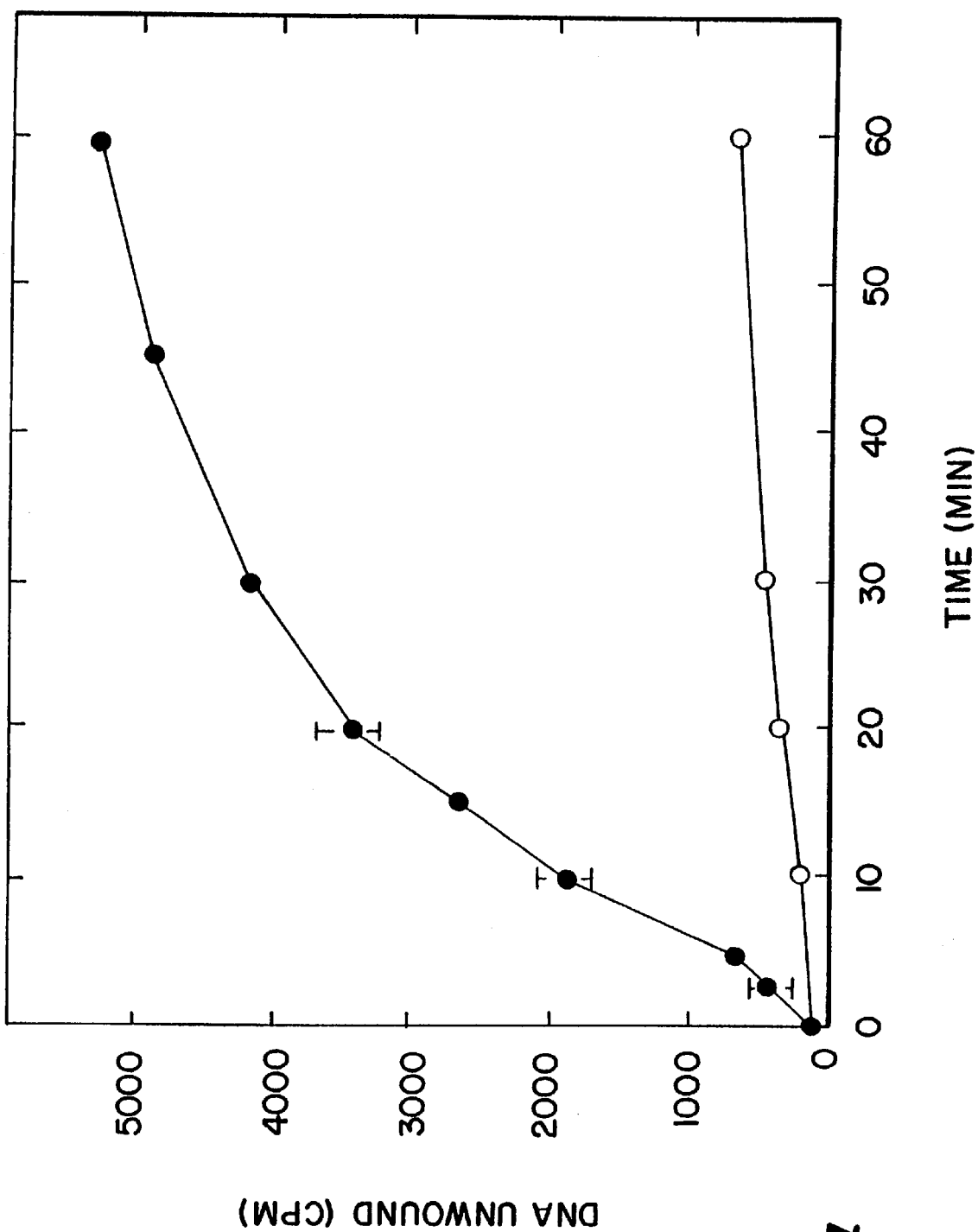
FIG. 4. Helicase activity is proportional to reaction time in the solid phase helicase assay. Helicase assays were performed and results quantitated with avidin-derivatized plates. Helicase assays were assembled in Buffer C with 6.8 pmol of the HSV-1 helicase-primase holoenzyme per reaction (●) or in Buffer C without ATP (○) to determine background values. Results are the mean±standard error of triplicate samples.

Immobilized duplex DNA molecules are substrates for the HSV-1 helicase-primase. To characterize the ability of the HSV-1 helicase-primase to unwind adsorbed helicase substrate increasing amounts of the HSV-1 helicase-primase were added to M13mp19/$^{33}$P-labeled 68-mer coated wells (FIG. 3). A linear dependence between the addition of the HSV-1 helicase-primase and the amount of product released from adsorbed surfaces was found. Moreover, the catalytic release of helicase reaction products displayed an absolute dependence on the addition of ATP. The time dependence of the helicase reaction was also examined using optimal enzyme concentrations (FIG. 4). Release of the 68-mer helicase reaction product was linear to about 30 min. After 30 min, there was a notable decrease in the rate of product release in the helicase reactions. This may be due to time-dependent denaturation of the helicase enzyme. Alternatively, the products of the helicase reaction may be partially depleted or may act as competitive inhibitors to prevent further progress of the unwinding reaction (9).

Example 5

Figure 5:
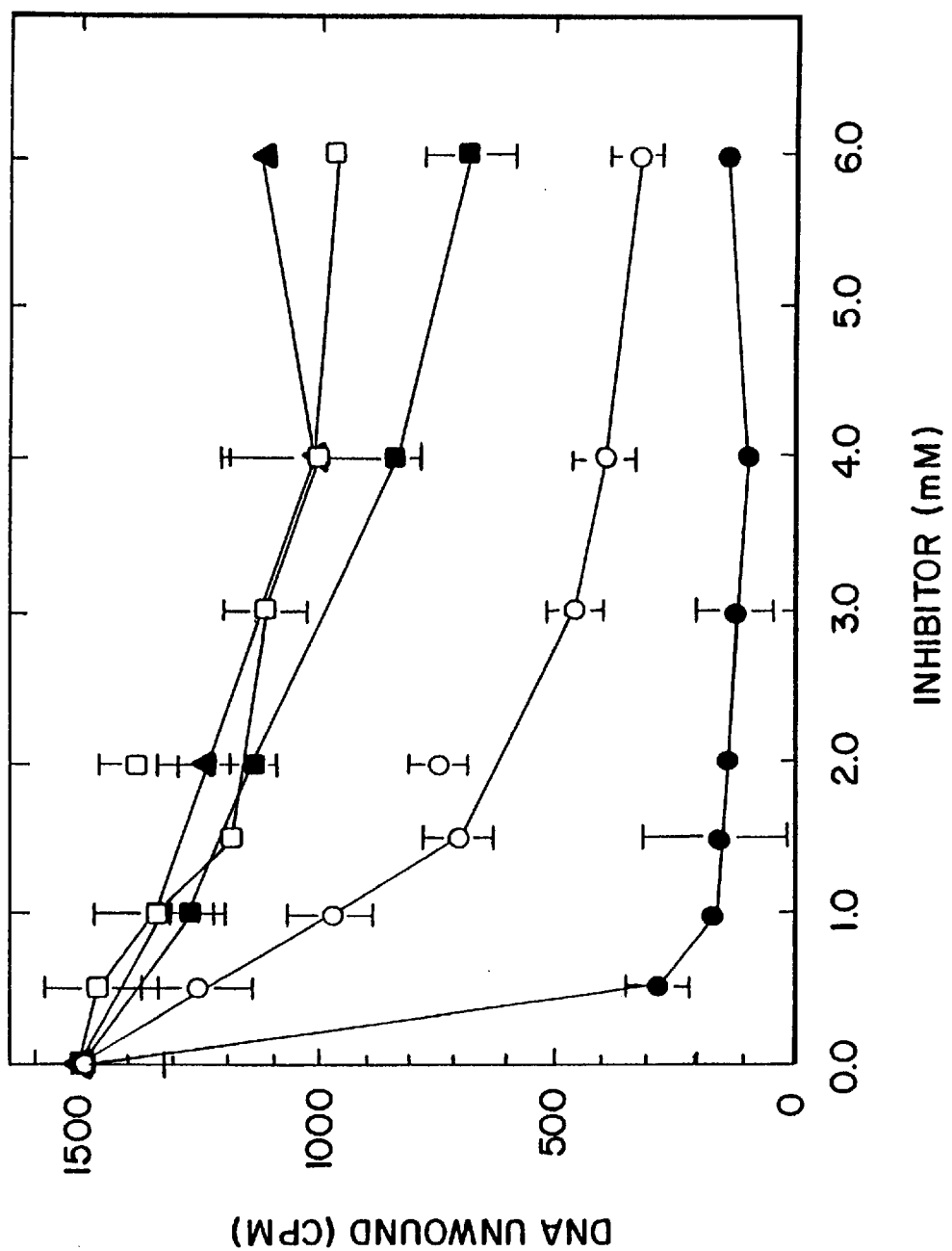
FIG. 5. Helicase activity of the HSV-1 helicase-primase is prevented by non-specific enzyme inhibitors. Helicase assays were performed and results quantitated with avidin-derivatized plates. Assays were assembled in triplicate with 6.8 pmol HSV-1 helicase-primase holoenzyme per reaction in the presence of the indicated nucleoside derivative. Reactions were allowed to proceed for a period of 20 min. prior to termination and quantitation. Either ATPγS,(●); ADP, (○); ADPβS, (■); AMPPNP, (□); AMPPCP, (Δ) was added at the indicated concentrations. A background value of 299 cpm (standard error=54 cpm, n=3) was subtracted from individual data points prior to the calculation of means and standard errors.

Analysis of potential nucleoside-based inhibitors of the HSV-1 helicase-primase holoenzyme. To display the utility of the solid phase helicase assay, I analyzed several commonly available nucleotides for inhibitory activity against the HSV-1 helicase-primase holoenzyme. AMPPCP, AMPPNP, ADPβS, ADP, or ATPγS were titrated in the assays designed to detect inhibitor activity (FIG. 5). AMP-PCP and AMPPNP were not effective inhibitors of the helicase activity of the HSV-1 helicase-primase. ADPβS inhibited activity by approximately 50% at the highest concentration analyzed (6.0 mM). ADP and ATPγS were the most effective enzyme inhibitors. I found concentrations of 1.5 to 2.0 mM ADP and less than 0.5 mM ATPγS capable of inhibiting the helicase activity of the HSV-1 helicase-primase by at least 50%.

Figure 6:
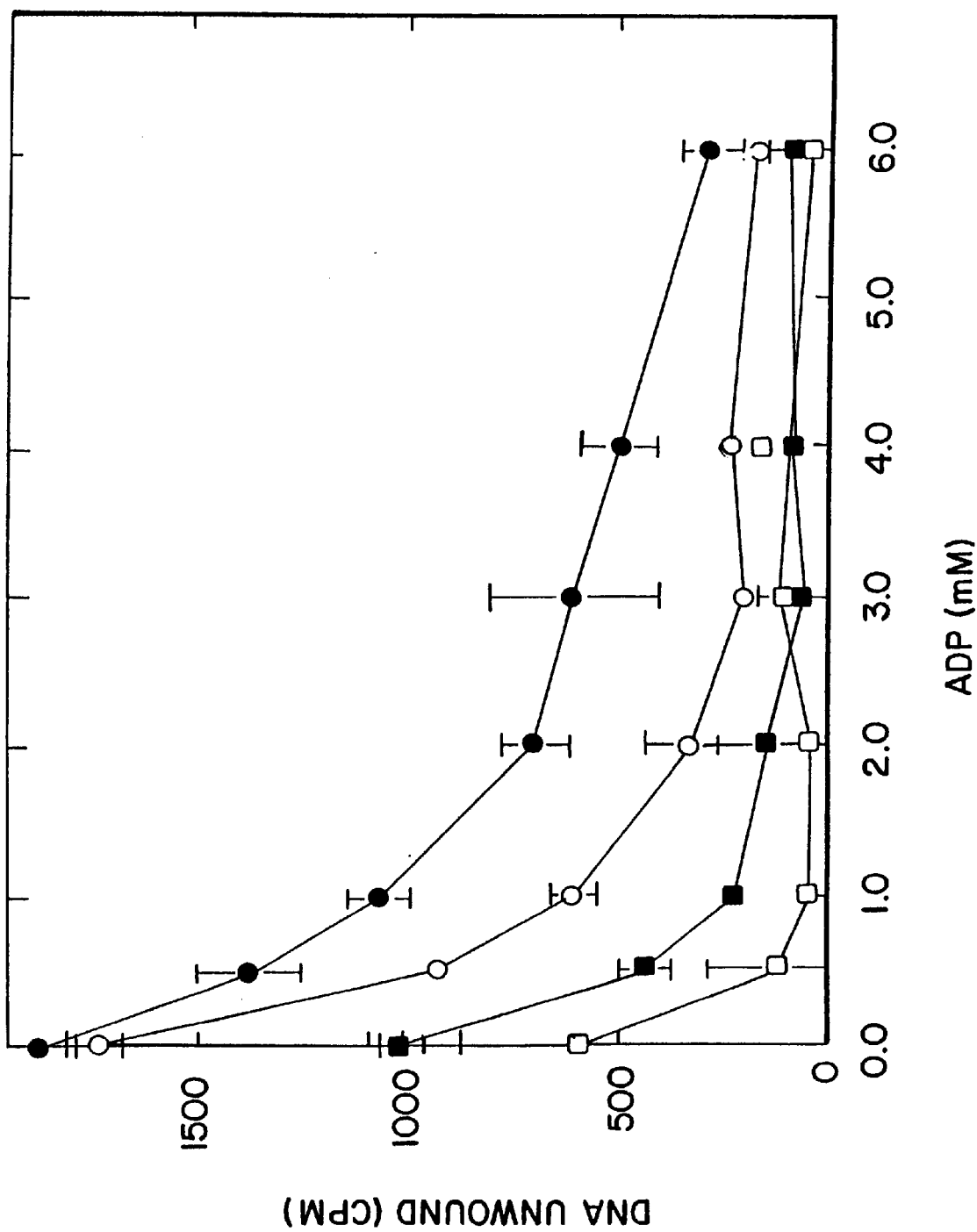
FIG. 6. Inhibition of the NTP-driven helicase activity of the HSV-1 helicase-primase by ADP. Helicase assays were performed and results quantitated with 6.8 pmol HSV-1 helicase-primase holoenzyme per reaction in the presence of the indicated nucleoside avidin-derivatized plates except that Buffer C contained 4.0 mM of one of the nucleoside triphosphates indicated below to drive the helicase reactions. ADP was added as a non-specific nucleoside helicase inhibitor at the indicated concentrations. A background value of 368 cpm (standard error=44 cpm, n=11) was subtracted from each point prior to the determination of means and standard errors. Helicase assays contained ATP (●), GTP (○), CTP (■), or UTP (□).

The ability of ADP to inhibit the helicase of the HSV-1 helicase-primase was analyzed further by examining helicase reactions driven by nucleoside triphosphates other than ATP (FIG. 6). GTP was nearly as effective at promoting helicase-mediated unwinding as ATP. CTP and UTP were less effective at promoting the helicase reaction; CTP was approximately half as effective as ATP and UTP slightly less effective than CTP. When nucleoside triphosphates other than ATP were used to drive helicase reactions, sensitivity to ADP inhibition was enhanced. GTP, CTP and UTP-driven helicase reactions were all inhibited to a greater extent by ADP when compared to the ATP-driven reaction. Essentially, the better the nucleoside triphosphates supported helicase activity, the less sensitive the activity was to ADP inhibition. This supports the observation that the mechanism by which nucleoside inhibitors of helicase activity mediate inhibition is competitive with respect to nucleoside triphosphate binding.

References Cited

1. Baker, T. A. and Kornberg, A. (1992) DNA Replication, Second Edition, W. H. Freeman and Company, New York.
2. Abdel-Monem M., Durwald, H., and Hoffmann-Berling, H. (1976) Eur. J. Biochem. 65, 441–449.
3. Venkatesan, M., Silver, L. L., and Nossal, N. G. (1982) J. Biol. Chem. 257, 12426–12434.
4. Matson, S. W., Tabor, S., and Richardson, C. C. (1983) J. Biol. Chem. 258, 14017–14024.
5. Helicase [$^3$H]Scintillation Proximity Assay Enzyme Assay System, Product Specification Document (1996) Amersham Life Science, Arlington Heights, Ill.
6. Houston, P., and Kodadek, T. (1994) Proc. Natl. Acad. Sci. USA 91, 5471–5474.
7. Raney, K. D., Sowers, L. C., Millar, D. P., and Benkovic, S. J. (1994) Proc. Natl. Acad. Sci. USA 91, 6644–6648.
8. Eggleston, A. K., Rahim, N. A., and Kowalczykowski, S. C. (1996) Nucleic Acids Res. 24, 1179–1186.
9. Crute, J. J., Mocarski, E. S., and Lehman, I. R. (1988) Nucleic Acids Res. 16, 6585–6596.
10. Dracheva, S., Koonin, E. V., and J. J. Crute. Identification of the primase active site of the herpes simplex virus type 1 helicase-primase. (1995) J. Biol. Chem. 270: 14148–14153.
11. Dodson, M. S., Crute, J. J., Bruckner, R. C., and Lehman, I. R. (1989) J. Biol. Chem. 264, 20835–20838.

While I have described a number of embodiments of this invention, it is apparent that my basic constructions may be altered to provide other embodiments that utilize the products and processes of this invention. Therefore, it will be appreciated that the scope of this invention is to be defined by the appended claims, rather than by the specific embodiments which have been presented by way of example.

I claim:

1. A method for measuring the helicase inhibiting ability of a test substance comprising the steps of:

(a) immobilizing on a solid support under acid pH conditions a helicase substrate comprising a single stranded nucleic acid polymer hybridized to a labeled helicase reaction product, wherein the labeled helicase reaction product is detectable in solution by helicase activity;
    (b) contacting the immobilized helicase substrate with a test substance to produce a reaction premix;
    (c) contacting under neutral or slightly alkaline pH conditions the reaction premix of step (b) with a helicase capable of releasing labeled helicase reaction product into solution by helicase activity; and
    (d) measuring the amount of labeled helicase reaction product released into solution as a function of time.

2. The method according to claim 1, wherein the labeled helicase reaction product comprises a hybridizing nucleic acid sequence optionally flanked by non-hybridizing sequences on its 5' and 3' end.

3. The solid phase helicase assay according to claim 2, wherein the hybridizing nucleic acid sequence comprises from 10–50 nucleotides and each of the non-hybridizing sequences comprises from 10–80 nucleotides.

4. The method according to claim 1, wherein the solid support is a protein-derivatized polystyrene microtiter well plate.

5. The method according to claim 4, wherein the protein is avidin.

6. The method according to claim 1, wherein the labeled helicase reaction product is radiolabeled.

7. The method according to claim 1, wherein the helicase is a herpes virus helicase-primase.

8. The method according to claim 7, wherein the herpes virus helicase-primase is the HSV-1 helicase-primase.

9. The method according to claim 8, wherein the model helicase substrate is M13mp19 single-stranded DNA hybridized with a $^{33}$P-labeled helicase reaction product.

10. The solid phase helicase assay according to claim 1, wherein in step (a) the helicase substrate is immobilized on a solid support under acid pH of about 3.25 to 4.0.

* * * * *